(12) United States Patent
Begg

(10) Patent No.: US 11,096,569 B2
(45) Date of Patent: Aug. 24, 2021

(54) ENDOSCOPE WITH A MULTIPLE DIAMETER WORKING SECTION

(71) Applicant: COVIDIEN LP, Mansfield, MA (US)

(72) Inventor: Nikolai David Begg, Wayland, MA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 14/883,754

(22) Filed: Oct. 15, 2015

(65) Prior Publication Data

US 2016/0106309 A1 Apr. 21, 2016

Related U.S. Application Data

(60) Provisional application No. 62/184,621, filed on Jun. 25, 2015, provisional application No. 62/064,176, filed on Oct. 15, 2014.

(51) Int. Cl.
*A61B 1/313* (2006.01)
*A61B 1/002* (2006.01)
(Continued)

(52) U.S. Cl.
CPC .............. *A61B 1/313* (2013.01); *A61B 1/002* (2013.01); *A61B 1/00066* (2013.01);
(Continued)

(58) Field of Classification Search
CPC . G02B 23/2476; A61B 1/313; A61B 1/00066; A61B 1/00096; A61B 1/303;
(Continued)

(56) References Cited

U.S. PATENT DOCUMENTS 3,257,902 A * 6/1966 Hopkins ................ A61B 1/055
359/363
4,046,140 A * 9/1977 Born ........................ A61B 1/04
600/184
(Continued)

FOREIGN PATENT DOCUMENTS

CN 1972626 A 5/2007
CN 101394779 A 3/2009
(Continued)

OTHER PUBLICATIONS

Chinese Office Action issued in corresponding application No. 201580055766.2 dated Jul. 2, 2018 with English translation, 17 pages.
(Continued)

*Primary Examiner* — Timothy J Neal
*Assistant Examiner* — Jae Woo
(74) *Attorney, Agent, or Firm* — Carter, DeLuca & Farrell

(57) ABSTRACT

An endoscope having a multiple diameter working section is disclosed. The endoscope includes a housing, a working section, and a rod-lens optical system. The housing is at a proximal end of the endoscope. The working section is integral with and extends from the housing. The working section includes at least a first section and a second section. The first section is contiguous to the housing, and the second section is at a distal end of the endoscope. The rod-lens optical system is positioned at least partially in the first section of the working section and at least partially in the second section of the working section. The endoscope is defined such that the outer diameter of the first section is larger than the outer diameter of the second section.

13 Claims, 12 Drawing Sheets

(51) Int. Cl.
*A61B 1/303* (2006.01)
*A61B 1/00* (2006.01)
*G02B 23/24* (2006.01)
*A61B 1/018* (2006.01)

(52) U.S. Cl.
CPC ...... *A61B 1/00071* (2013.01); *A61B 1/00078* (2013.01); *A61B 1/00096* (2013.01); *A61B 1/303* (2013.01); *G02B 23/2476* (2013.01); *A61B 1/00094* (2013.01); *A61B 1/00135* (2013.01); *A61B 1/00195* (2013.01); *A61B 1/018* (2013.01)

(58) Field of Classification Search
CPC . A61B 1/002; A61B 1/00078; A61B 1/00071; A61B 1/00195; A61B 1/018; A61B 1/00135; A61B 1/00094
See application file for complete search history.

(56) References Cited

U.S. PATENT DOCUMENTS

| | | | | |
|---|---|---|---|---|
| 4,178,920 A * | 12/1979 | Cawood, Jr. | ........... | A61B 1/307 600/107 |
| 4,350,147 A | 9/1982 | Sarrine | | |
| 4,449,532 A * | 5/1984 | Storz | ................. | A61B 1/00154 600/114 |
| 4,557,255 A * | 12/1985 | Goodman | .............. | A61B 1/307 600/104 |
| 4,615,333 A * | 10/1986 | Taguchi | ............. | A61B 1/00165 359/737 |
| 4,779,613 A * | 10/1988 | Hashiguchi | ........ | A61B 1/00179 359/512 |
| 4,807,595 A | 2/1989 | Hiltebrandt | | |
| 5,083,549 A * | 1/1992 | Cho | ................... | A61B 1/00071 600/108 |
| 5,290,294 A * | 3/1994 | Cox | ...................... | A61B 1/307 600/104 |
| 5,505,686 A * | 4/1996 | Willis | ................ | A61B 1/00087 600/104 |
| 5,512,034 A * | 4/1996 | Finn | ................... | A61B 1/00089 600/138 |
| 5,584,793 A * | 12/1996 | Sauer | ................. | A61B 1/00101 206/370 |
| 5,647,840 A * | 7/1997 | D'Amelio | .......... | A61B 1/00091 600/169 |
| 5,735,792 A * | 4/1998 | Vanden Hoek | .... | A61B 1/00087 600/138 |
| 5,825,534 A * | 10/1998 | Strahle | ............... | A61B 1/00179 359/376 |
| 5,857,961 A * | 1/1999 | Vanden Hoek | .... | A61B 1/00165 600/104 |
| 6,201,649 B1 * | 3/2001 | Rudischhauser | ...... | G02B 7/025 359/808 |
| 6,325,065 B1 | 12/2001 | Rabiner | | |
| 8,740,773 B2 * | 6/2014 | Kucklick | ............... | A61B 1/317 600/114 |
| 9,700,378 B2 * | 7/2017 | Mowlai-Ashtiani | ........................ | A61B 1/00135 |
| 2002/0072712 A1 * | 6/2002 | Nool | ................. | A61M 25/0136 604/167.01 |
| 2002/0095065 A1 | 7/2002 | Kamrava | | |
| 2003/0130565 A1 | 7/2003 | Muller | | |
| 2007/0129757 A1 * | 6/2007 | Armstrong | ........... | A61B 5/6851 606/213 |
| 2007/0185380 A1 * | 8/2007 | Kucklick | ........... | A61B 1/00135 600/114 |
| 2008/0082000 A1 | 4/2008 | Thoms | | |
| 2009/0040606 A1 * | 2/2009 | Lee | .................... | A61B 1/00193 359/476 |
| 2009/0048685 A1 * | 2/2009 | Frigstad | ........... | A61B 17/12022 623/23.76 |
| 2009/0137970 A1 | 5/2009 | Samuel et al. | | |
| 2009/0292168 A1 * | 11/2009 | Farr | ..................... | A61B 1/0607 600/109 |
| 2009/0318765 A1 | 12/2009 | Yuuichi | | |
| 2010/0081875 A1 * | 4/2010 | Fowler | ............... | A61B 1/00149 600/114 |
| 2010/0123950 A1 * | 5/2010 | Fujiwara | ................ | A61B 1/002 359/368 |
| 2011/0061659 A1 * | 3/2011 | Cruzada | .................. | A61F 6/225 128/831 |
| 2011/0224492 A1 * | 9/2011 | Stern | ..................... | A61B 1/018 600/153 |
| 2012/0029280 A1 * | 2/2012 | Kucklick | .................. | A61B 1/05 600/109 |
| 2013/0274550 A1 | 10/2013 | Takeuchi | | |
| 2013/0281782 A1 * | 10/2013 | Zhou | .................. | A61B 1/00078 600/125 |
| 2014/0048074 A1 * | 2/2014 | Tai | ............................ | A61F 6/18 128/833 |
| 2014/0187860 A1 * | 7/2014 | Yang | .................. | A61B 1/00071 600/114 |
| 2014/0200402 A1 | 7/2014 | Snoke et al. | | |
| 2014/0316199 A1 * | 10/2014 | Kucklick | ............... | A61B 1/015 600/109 |
| 2014/0350344 A1 * | 11/2014 | Vogel | ................. | A61B 1/00112 600/130 |
| 2014/0378753 A1 * | 12/2014 | Buster | .................. | A61B 17/435 600/33 |
| 2015/0374400 A1 * | 12/2015 | Kumar | ........... | A61B 17/320016 606/110 |

FOREIGN PATENT DOCUMENTS

| | | |
|---|---|---|
| CN | 102068232 A | 5/2011 |
| DE | 8634860 U1 | 6/1988 |
| DE | 8806359 U1 | 7/1988 |
| DE | 202005009189 U1 | 9/2005 |
| DE | 112012000216 T5 | 8/2013 |
| JP | 55030109 | 2/1980 |
| JP | 2011167460 A | 9/2011 |
| WO | 2005037088 A2 | 4/2005 |
| WO | 2005110206 A1 | 11/2005 |

OTHER PUBLICATIONS

Chinese Office Action issued in corresponding Chinese Application No. 201580055766.2 dated Mar. 11, 2019 with English translation, 12 pages.
European Examination Report issued in corresponding European Application No. 15790341.0 dated Jan. 16, 2019, 3 pages.
Japanese Office Action issued in Japanese Application No. 2017-519866 dated Jun. 12, 2019, 9 pages.
Australian Examination Report issued in corresponding 2015332475 dated Jun. 25, 2019, 3 pages.
Office Action issued in corresponding Indian Appl. No. 201717009201 dated Aug. 24, 2020 (7 pages).
Chinese Office Action issued in corresponding Appl. No. CN 201580055766.2 dated Sep. 17, 2019 (6 pages).
Japanese Office Action issued in corresponding Appl. No. JP 2017-519866 dated Dec. 2, 2019, together with English language translation (7 pages).

* cited by examiner

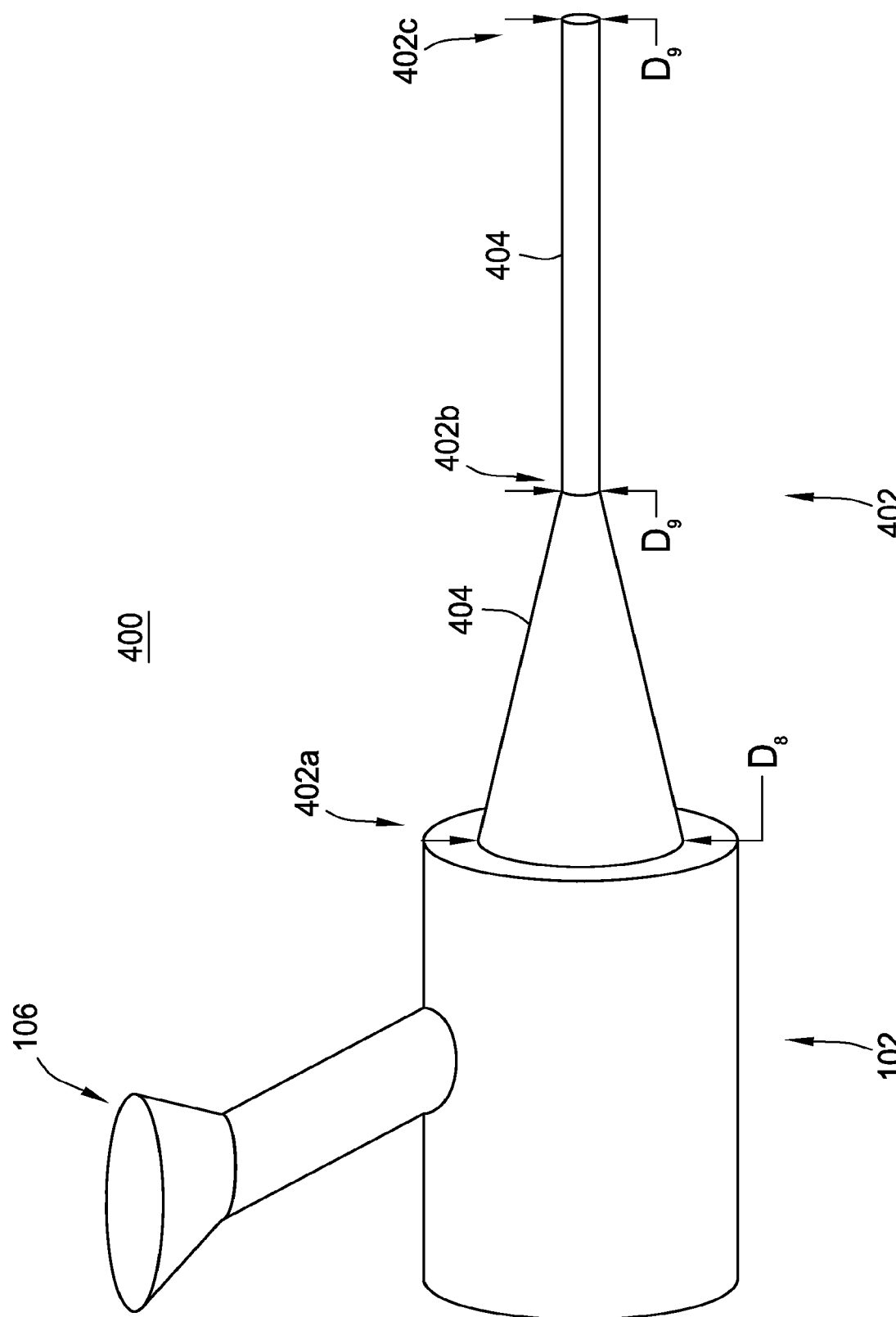

ENDOSCOPE WITH A MULTIPLE DIAMETER WORKING SECTION

CROSS-REFERENCE TO RELATED APPLICATION

This application is related to U.S. Provisional Application No. 62/064,176, filed Oct. 15, 2014, titled, "Endoscope With Multiple-Diameter Working Section," which is hereby incorporated herein by reference in its entirety, and U.S. Provisional Application No. 62/184,621, filed Jun. 25, 2015, titled, "Endoscope With Multiple-Diameter Working Section," which is hereby incorporated herein by reference in its entirety.

BACKGROUND

An endoscope is an instrument that is inserted into a subject (e.g., patient during a medical procedure) under the control of a user (e.g., physician, clinician, technician, operator, etc.) for the user to view inside the subject, among other purposes. The distal section of the endoscope, also referred to as the working section, is the section of the endoscope that is inserted into the subject. Insertion may be through a cannula (e.g., a sheath) or other instrument, or may be directly into the patient through an orifice or incision.

In general, endoscopes are configured to have longer lengths and smaller diameters in an effort to reach deeper into subjects while reducing the associated discomfort. However, when inside the subject, manipulation of the endoscope applies radial forces to the working section. Such radial forces can cause the working section to bend or flex. For a constant radial force applied to a tip of the working section, the tip will deflect relatively more if the length of the working section is increased or if the diameter of the working section is decreased.

The endoscope may house components and/or accept instruments therethrough to enable the user to view into the patient and/or perform medical procedures within the patient. Bending or flexing of the working section during such procedures can transmit the above-described radial forces to the components and/or instruments within the working section. The components and/or instruments may have certain tolerances to bending or flexing that, if exceeded, can cause the components and/or instruments to fail. Therefore, a tradeoff exists between (1) the desire to increase the length and/or decrease the diameter of the working section to cause minimal discomfort when inserted into the patient and (2) the desire to prevent or at least reduce bending and/or flexing of the working section to reduce the chances of causing components and/or instruments therein to fail (e.g., break, snap, deform, etc.).

Thus, a need exists for an endoscope having a working section with a length and a diameter that provide for access within a subject patient with reduced discomfort, while reducing bending/flexing of the working section of the endoscope. The present disclosure is directed to these and other needs.

SUMMARY

In an embodiment, an endoscope comprising: a proximal end; a distal end; a housing at the proximal end of the endoscope; a working section coupled to and extending from the housing, the working section comprising a first section contiguous to the housing and a second section at the distal end of the endoscope, wherein an outer diameter of the first section is larger than an outer diameter of the second section; and an optical system positioned at least partially in the first section of the working section and at least partially in the second section of the working section.

In an alternate embodiment, an endoscope comprising: a housing; a working section extending from the housing and having an outer surface, the outer surface having a proximal end and a distal end, the proximal end is contiguous to the housing and having a first diameter, and the distal end having a second diameter, the first diameter is larger than the second diameter; and an optical system positioned in the working section such that the optical system extends between the proximal and distal ends of the working section.

In an embodiment, a method of performing a surgical procedure, comprising: disposing a working section of an endoscope into a body cavity, wherein the endoscope comprises a proximal end and a distal end, wherein a housing is disposed at the proximal end of the endoscope, and wherein the working section is coupled to and extends from the housing and comprises a first section and a second section, wherein the first section is contiguous to the housing, wherein the second section is at the distal end of the endoscope, an outer diameter of the first section is larger than an outer diameter of the second section, wherein an optical system is disposed at least partially in the first section of the working section and at least partially in the second section of the working section; performing, while at least a portion of the working section is disposed in the body cavity, at least a portion of a surgical procedure.

BRIEF DESCRIPTION OF THE DRAWINGS

The disclosure will be better understood from the following description of exemplary embodiments together with reference to the accompanying drawings, in which:

FIG. 4A shows a perspective view of an endoscope with a partially and uniformly tapered working section, according to certain embodiments of the present disclosure;

Figure 1:
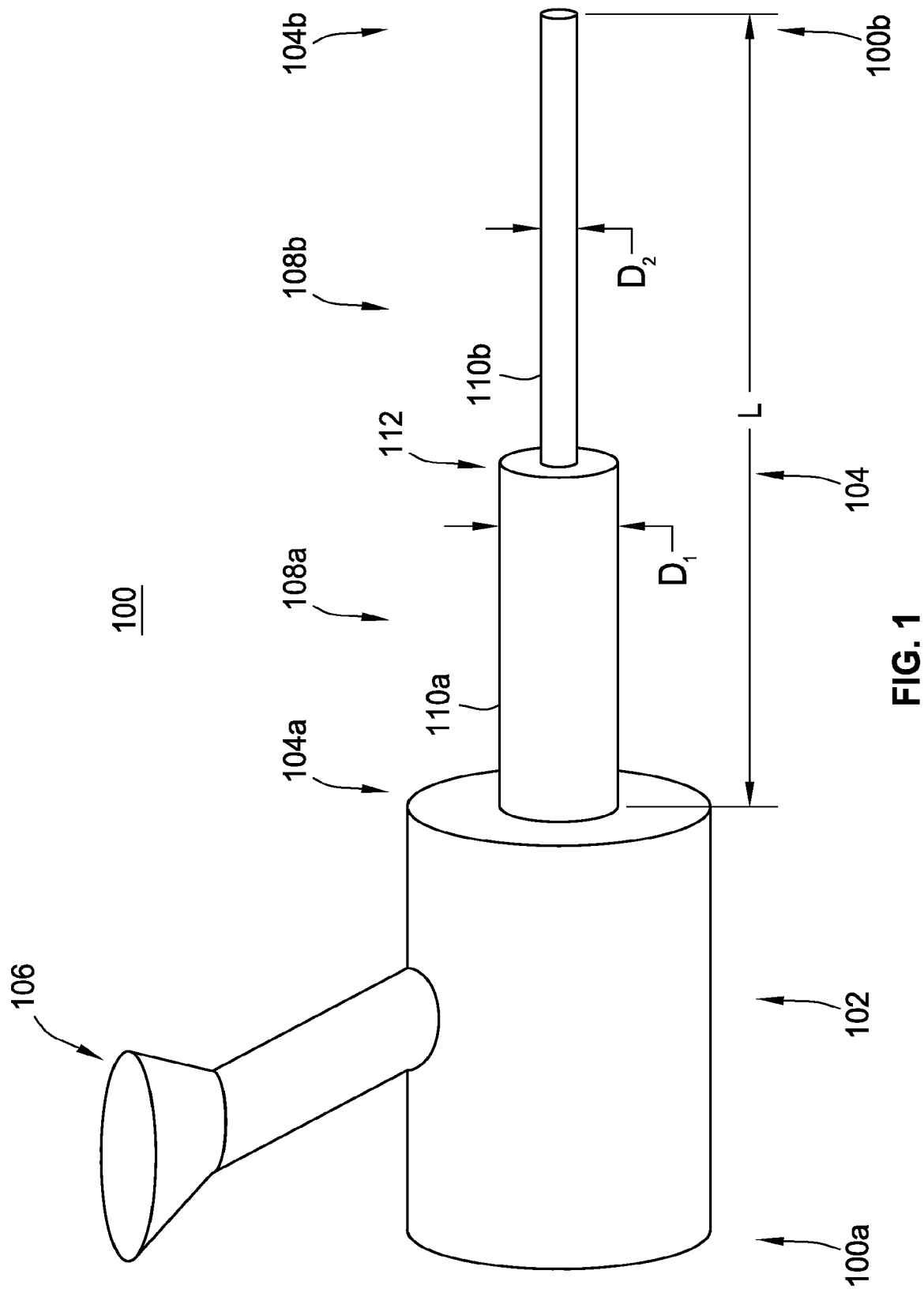
FIG. 1 shows a perspective view of an endoscope with a multiple diameter working section, according to certain embodiments of the present disclosure.

While the disclosure is susceptible to various modifications and alternative forms, specific implementations thereof have been shown by way of example in the drawings and will be described in detail herein. It should be understood, however, that it is not intended to limit the disclosure to the particular forms disclosed, but on the contrary, the intention is to cover all modifications, equivalents, and alternatives falling within the spirit of the present disclosure.

DEFINITIONS

"Working section" shall mean a portion of an endoscope is the section of the endoscope that is inserted into a patient. Since surgical techniques may vary, for example, based on the surgeon as well as the patient and the surgical procedure, the term "working section" is used herein to describe the portion of the endoscope designed for insertion in a patient for some or all of the duration of a procedure regardless of whether a practitioner in every scenario with every patient would insert it in precisely the same manner or for exactly the same duration. Thus, the working sections are designed to account for human variation both in the practitioner and the patient.

"Working length" shall mean a length of the working section, and it will be apparent to one skilled in the art which working length is appropriate for particular procedures and/or patients. Therefore, in some embodiments, some or all of the working length of a working section may be inserted into a patient at the start of a procedure, for example, for dilation purposes, at the end or a procedure, or for any portion of the duration of the procedure.

"Inflexible," in reference to an optical system, shall mean a system that is semi-rigid or stiff (e.g., intended to resist bending during use), but shall not necessarily require a completely rigid system. Likewise, a "flexible" optical system may comprise a system that is intended to be bent during use.

"About" in reference to measurement shall the stated measurement +/−5% of the stated measurement.

Whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent.

DESCRIPTION

This disclosure is susceptible of implementation in many different forms. There are shown in the drawings, and will herein be described in detail, representative implementations with the understanding that the present disclosure is to be considered as an exemplification of the principles of the present disclosure and is not intended to limit the broad aspects of the disclosure to the implementations illustrated.

The subject technology is directed to an endoscope that includes a working section at the distal end. Some applications of an endoscope may comprise a method where the working section first passes through a large orifice/incision or canal (e.g., vagina) before reaching a small orifice or canal (e.g., cervical os) inside the patient. In such applications, a proximal portion of the working section may not pass through the small orifice (e.g., cervical os). Therefore, according to some aspects of the present disclosure, an endoscope is disclosed that leverages the foregoing steps in the anatomical diameters of the orifices, incisions, and/or canals inside a patient to increase at least a portion of the outer diameter(s) of proximal section(s) of the working section. By increasing the outer diameter(s) of proximal section(s) of the working section, particularly while keeping the length of the working section constant, the length of the smallest diameter section at the distal end of the working section can be decreased. The decrease in the length of the smallest diameter section enables the diameter of the section to also decrease while maintaining or even reducing the amount of bending and/or flexing of the section in response to a given force. The smaller diameter of the distal section enables insertion of the distal section into a distal orifice and/or canal (e.g., cervical os) of a patient with reduced trauma and/or discomfort as compared to a relatively larger diameter working section. In addition, by decreasing the "bending length," that is, the length of the scope that may be subject to bending during use, the opportunity to use different and/or better quality optics devices is enabled since the distal insertable length (working length) is reduced without compromising the entire device including the optics. Thus, using methods, materials, systems, and apparatuses discussed herein, at least the optical performance of an endoscope may be improved.

FIG. 1 shows a perspective view of an endoscope 100, according to certain embodiments of the present disclosure. The endoscope 100 includes two sections: the handle 102 (also referred to herein as a housing of the endoscope 100) and the working section 104. According to some implementations, the handle 102 and the working section 104 can be formed as two separate pieces that are fixed together. The handle 102 and the working section 104 can be permanently fixed, such as by welding, or selectively fixed, such as by the working section 104 being screwed into the handle 102 prior to being used during a medical procedure. According to some implementations, the handle 102 and the working section 104 are formed as a single monolithic piece. According to the foregoing, the handle 102 and the working section 104 are mechanically coupled together during a medical procedure and effectively form a single piece.

The handle 102 and the working section 104 can be formed of various materials used within the endoscopy and/or surgical arts to form inflexible components that are resistant to being bent. The handle 102 and, more particularly, the working section 104 are configured to reduce or prevent bending/flexing that may cause components and/or instruments within the handle 102 and/or the working section 104 to fail (e.g., break, snap, deform, etc.). The handle 102 and the working section 104 can be formed of the same material or of two or more different materials. Such materials include various plastics, metals, and/or alloys. By way of example, the handle 102 and the working section 104 can be formed of a single, monolithic piece of surgical grade stainless steel. Alternatively, the handle 102 and the working section 104 can be formed as two separate surgical grade stainless steel pieces that are then joined together as a single monolithic piece, such as by welding, press fitting, screwing, riveting, gluing, etc.

The working section 104 is designed to resist being bent in response to applied forces (e.g., during insertion into a patient's vagina and/or cervical os). However, certain amounts of force may still cause the working section 104 to bend and/or flex by a relatively small amount. According to some implementations, the working section 104 is such that any portion of a central axis of the working section 104 bends and/or flexes no more than ten degrees compared to a non-bent state (e.g., horizontal). According to some other implementations, the working section 104 is such that any portion of the central axis of the working section 104 bends and/or flexes no more than five degrees compared to a non-bent state (e.g., horizontal). According another implementation, the working section 104 is such that any portion of the central axis of the working section 104 bends and/or flexes no more than two degrees compared to a non-bent state (e.g., horizontal). According another implementation, the working section 104 is such that any portion of the central axis of the working section 104 bends and/or flexes no more than one degree compared to a non-bent state (e.g., horizontal). According another implementation, the working section 104 is such that any portion of the central axis of the working section 104 bends and/or flexes no more than half of one degree compared to a non-bent state (e.g., horizontal). The amount of bending and/or flexing is at least partially dependent upon and can vary based on the amount of and location of applied force(s) to the working section 104 during operation. Further, the amount of bending and/or flexing is at least partially dependent upon and can vary based on the materials (e.g., surgical grade stainless steel, etc.) of the working section 104 and/or the dimensions (e.g., diameter, length, etc.) of the working section 104.

The handle 102 is located at a proximal end 100a of the endoscope 100. The handle 102 enables a user to grasp and manipulate the endoscope 100, such as during a procedure. The handle 102 can include one or more additional features or elements, such as the optical port 106, which provides for additional functionality of the endoscope 100. In the case of the optical port 106, the optical port 106 can couple with or include therein a rod-lens optical system (discussed below in further detail) that extends to a distal end 100b of the endoscope 100.

The working section 104 is the section of the endoscope 100 designed to be inserted into a patient during a procedure. For example, according to some implementations, the diameter or width of the handle 102 inhibits the user from inserting the handle 102 into a patient during a procedure (e.g., it physically will not fit into the patient). Additionally, or in the alternative, the length of the working section 104 inhibits and/or prevents the user from inserting the handle 102 into the patient during a procedure.

As shown in FIG. 1, the working section 104 has a length L. The length L of the working section 104 is established such that it enables a user to grasp and manipulate the handle 102 outside of the patient when the working section 104 is being inserted into or already inserted into the patient and accessing a surgical site (e.g., uterus) associated with a procedure. The length L of the working section 104 can vary depending on the specific procedure for which the endoscope 100 is designed. By way of example, an endoscope designed for hysteroscopy (e.g., hysteroscope) can have a working section 104 with a length L between about 140 and about 350 millimeters (mm). However, the working section 104 can have a variety of other lengths L such as, for example, the length L can be about 160 millimeters (mm), about 180 mm, about 200 mm, about 220 mm, about 240 mm, about 260 mm, about 280 mm, about 300 mm, about 320 mm, about 340 mm, etc. depending on the specific procedure for which the working section 104 and/or the endoscope 100 is designed.

In some cases working section 104 is round with one or more internal lumens to enable one or more components and/or instruments to be located therein and/or inserted therethrough. However, the geometry (e.g., cross-section) of the working section 104 can differ from being round without departing from the spirit and scope of the present disclosure, such as being tubular with a square cross-section, tubular with a triangular cross-section, tubular with an ovular cross-section, tubular with a "D-shaped" cross-section, etc. In the case where the endoscope 100 includes a rod-lens optical system, the working section 104 can include at least part of the rod-lens optical system to enable a user to view the inside of the patient (such as through the optical port 106) during a procedure. In addition to the rods-lens optical system, the working section 104 can include, for example, one or more instruments or components, such as a surgical cutting device for removing tissue via the endoscope 100, inflow and/or outflow instruments and/or channels for transporting fluid to and from the site, illumination fibers for transmitting light to illuminate the target anatomy, as well as, any other instruments and/or components found in the endoscopy and related arts.

As discussed herein, when an endoscope is inserted into a patient during a procedure, forces experienced at the distal end of the endoscope may cause the endoscope to bend and/or flex. The bending and/or flexing may cause damage and/or failure to instruments and/or components within the working section of the endoscope.

One component that may be found within an endoscope is an optical system, which may be flexible, inflexible, or a combination of both depending upon the section of the optics. An optical system enables a user to view inside the patient through the endoscope. Certain optical systems are designed to be inflexible because elements of such systems (e.g., lenses) are prone to damage and/or failure in response to applied forces that cause bending and/or flexing. An "inflexible" optical system as discussed herein may comprise a system that may be semi-rigid or stiff (e.g., intended to resist bending during use), but may not be a completely rigid system. A "flexible" optical system may comprise a system that is intended to be bent during use. A rod-lens optical system is one example of an inflexible optical system. The optical elements of a rod-lens optical system can fail if the housing of the rod-lens optical system (e.g., working section 104) bends and/or flexes beyond certain tolerances, which transmits forces to the optical elements. While flexible optical systems exist within the endoscopy arts that do not have the same tolerances to bending and/or flexing as inflexible optical systems, such as fiber optic bundles and miniaturized electronics allowing for "chip-on-a-stick" cameras, a rod-lens optical system, as one example of an inflexible optical system, provides relatively better image quality compared to such flexible optical systems. To reduce the effects of such forces and limit or prevent damage to instruments used with and/or components/elements of the endoscope 100, such as inflexible optical systems, the working section 104 of the endoscope 100 includes multiple sections with varying diameters.

As shown in FIG. 1, according to some implementations, the working section 104 can include two sections: a proximal section 108a and distal section 108b. The proximal section 108a (also referred to as the access section) is contiguous to the handle 102 and forms the proximal end 104a of the working section 104. In the endoscope 100 of FIG. 1, the distal section 108b (also referred to as the operative section) is contiguous to access section 108a and forms the distal end 104b of the working section 104.

The access section 108a has an outer surface 110a that has a diameter $D_1$. The operative section 108b also has an outer surface 110b that has a diameter $D_2$. Although described as two outer surfaces 110a and 110b, the working section 104 is formed as a single monolithic piece such that the outer surfaces 110a and 110b are formed integral to each other to increase the structural rigidity of the working section 104.

To achieve the multiple diameters of the working section 104, the diameter $D_1$ of the access section 108a is larger than the diameter $D_2$ of the operative section 108b, and the working section 104 includes a step 112 in the diameters of the outer surfaces 110a and 110b.

By having the working section 104 formed of the access section 108a and the operative section 108b with the different diameters, the working section 104 bends and/or flexes relatively less in response to a force applied to the distal end 104b (e.g., a force perpendicular to a central axis of the working section 104) for a given length L of the working section 104 as compared to, for example, a working section of length L that has a constant diameter equal to the diameter $D_2$ of the operative section 108b. By bending and/or flexing relatively less than a working section having the same length L and constant diameter equal to $D_2$, the working section 104 is less likely to cause damage to instruments and/or components/elements therein in response to forces being imparted on the working section 104.

Moreover, a working section that has a constant diameter can be thought of as having the smallest diameter along its entire length. In contrast, because of the step 112 (FIG. 1) in diameter from the access section 108a to the operative section 108b, the overall length of the smallest diameter of the working section 104 (i.e., operative section 108b) is relatively smaller compared to a constant diameter working section. By reducing the overall length of the smallest diameter portion of the working section 104 (i.e., compared to a constant diameter working section), the diameter $D_2$ of the operative section 108b can be further reduced while still exhibiting the same relative amount of bending and/or flexing in response to the same amount of force as an endoscope having a working section with a constant diameter across its entire length. That is, according to embodiments of the present disclosure, by providing part of the length L of the working section 104 with the relatively larger diameter access section 108a, the length of the smallest diameter operative section 108b is reduced, which enables the diameter $D_2$ to also be reduced without causing the operative section 108b to bend and/or flex more under the same amount of force. By allowing for the operative section 108b to have a smaller outer diameter 110b as compared to an endoscope with a working section having the same length L, the operative section 108b can be inserted into orifices (e.g., cervical os) within the patient that endoscopes cannot access because of the larger diameter and/or the operative section 108b can be inserted into orifices (e.g., cervical os) with less associated discomfort as compared to an endoscope inserted through the same orifice, all while exhibiting the same or less bending and/or flexing in response to radial forces on the operative section 108b.

Figure 2:
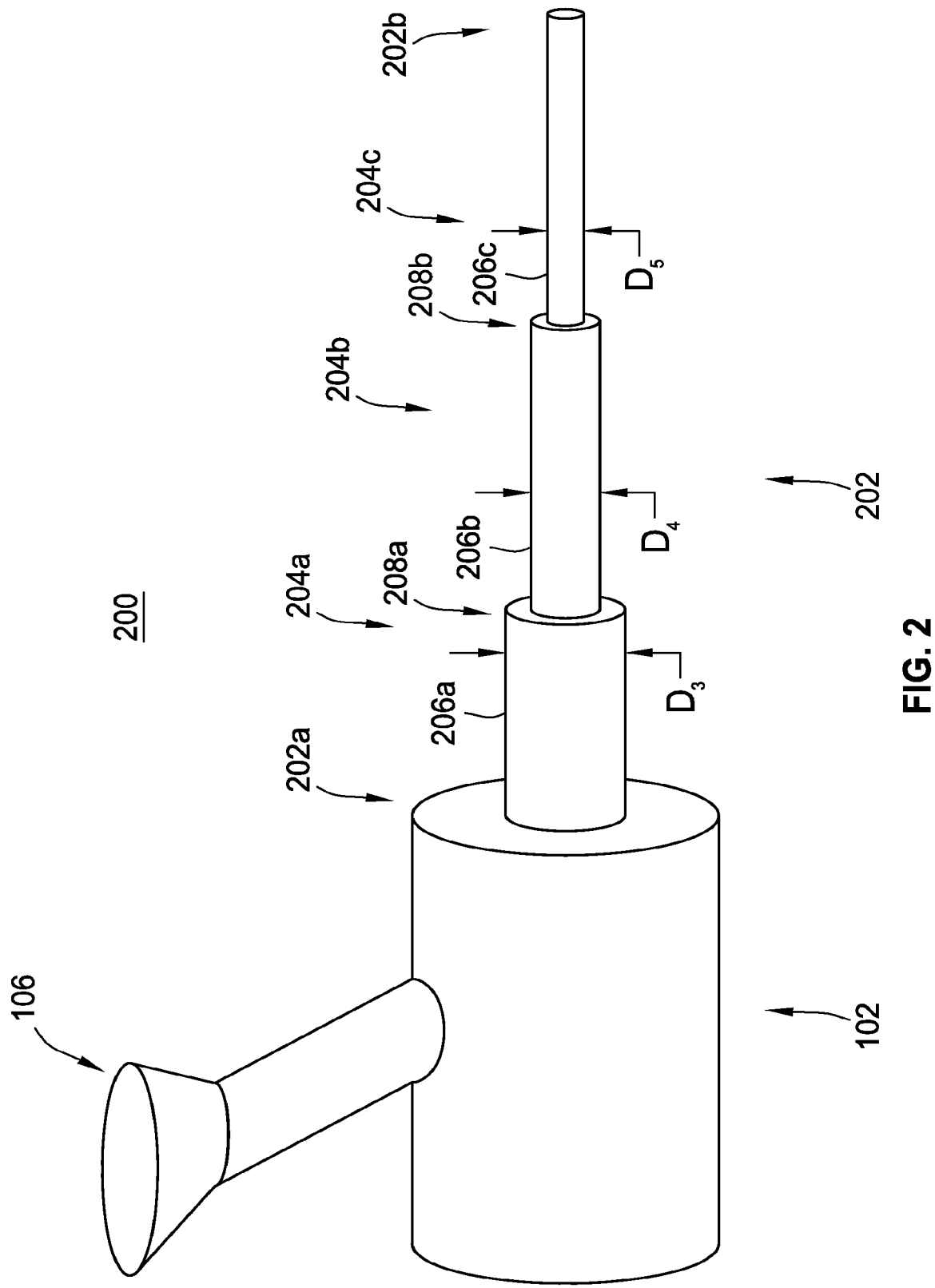
FIG. 2 shows a perspective view of an endoscope with a multiple diameter working section, according to certain embodiments of the present disclosure.

Referring to FIG. 2, FIG. 2 shows a perspective view of an endoscope 200, according to additional aspects of the present disclosure. The endoscope 200 is similar to the endoscope 100 of FIG. 1 but differs in that the endoscope 200 includes a working section 202 with more than one step in diameter. Specifically, instead of working section 104 of endoscope 100, endoscope 200 includes the working section 202 that includes a proximal section 204a, a middle section 204b, and a distal section 204c. Like access section 108a, the proximal section 202a is contiguous to the handle 102 and forms the proximal end 202a of the working section 202. Similar to the operative section 108b, the distal section 204c forms the distal end 202b of the working section 202. The middle section 204b is between and contiguous to the proximal section 204a and the distal section 204c. It is appreciated that one or more middle sections 204b may be employed, and that these middle sections may be of varying lengths and diameters, as discussed in detail below.

The example proximal section 204a has a round shape and an outer surface 206a that has a diameter $D_3$. The middle section 204b has a round shape and an outer surface 206b that has a diameter $D_4$. The distal section 204c has a round shape and an outer surface 206c that has a diameter $D_5$. Although described as three outer surfaces 206a-206c, the working section 202 may be formed as a single monolithic piece such that the outer surfaces 206a-206c are formed integral to each other to increase the structural rigidity of the working section 202.

To achieve the multiple diameters of the working section 202, the proximal section 204a, the middle section 204b, and the distal section 204c have progressively smaller diameters. Specifically, the diameter $D_3$ of the proximal section 204a is larger than the diameter $D_4$ of the middle section 204b, the diameter $D_4$ of the middle section 204b is larger than the diameter $D_5$ of the distal section 204c, and the working section 202 includes steps 208a and 208b in the diameters of the outer surfaces 206a-206c. By the working section 202 having the steps 208a and 208b in diameter, the working section 202 can extend into a patient the same distance as an endoscope while exhibiting less flexing and/or bending for the same length of the working section. Further, the distal end 202b of the working section 202 can have a smaller diameter than the distal ends of endoscopes while exhibiting the same or less flexing and/or bending for the same length of working section based on the length of the smallest diameter portion of the working section 202 being shorter than the length of the smallest diameter section of an endoscope (i.e., the entire length).

Although only one middle section 204b is shown and described with respect to FIG. 2, according to some implementations, the middle section 204b may include a plurality of middle sections of varying lengths, outer, and inner diameters. With a plurality of middle sections, outer diameters of the middle sections progressively decrease from a proximal middle section contiguous to the proximal section 204a to a distal middle section contiguous to the distal section 204c, to achieve the progressively smaller outer surfaces diameters of the middle sections.

Figure 3A:
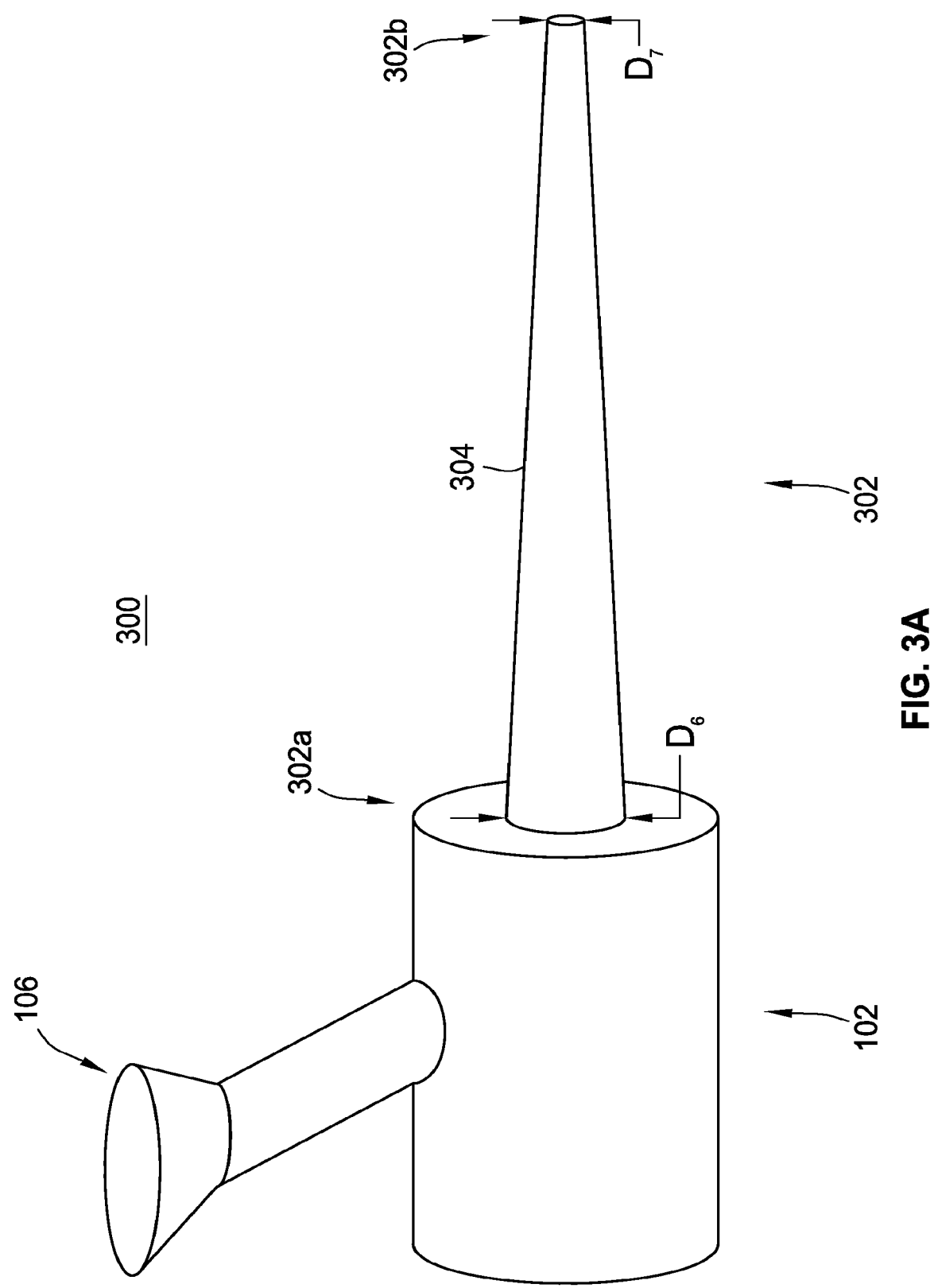
FIG. 3A shows a perspective view of an endoscope with a uniformly tapered working section, according to certain embodiments of the present disclosure.

Referring to FIG. 3A, FIG. 3A shows an endoscope 300 according to additional aspects of the present disclosure. The endoscope 300 is similar to the endoscope 100 of FIG. 1 but differs in that the endoscope 300 includes a tapered outer surface 304 of the working section 302. Specifically, the endoscope 300 includes the working section 302 that includes a proximal end 302a and a distal end 302b. The outer surface 304 of the working section 302 at the proximal end 302a has a diameter $D_6$, and the outer surface 304 of the working section 302 at the distal end 302b has a diameter $D_7$. The diameter $D_6$ at the proximal end 302a is greater than the diameter $D_7$ at the distal end 302b. Further, according to some implementations, and as shown in FIG. 3A, the working section 302 has a uniform taper from the proximal end 302a to the distal end 302b.

The working section 302 can have a smaller diameter $D_7$ at the distal end 302b as compared to a working section with a constant diameter of comparable length. For example, the diameter $D_6$ of the proximal end 302a of the working section 302 can be larger than the diameter of a working section, which enables a smaller diameter $D_7$ at the distal end 302b as compared to the working section of the same length. At the same time, the working section 302 bends and/or flexes less than or comparable to the working section having the same length with the constant diameter despite the working section 302 having the smaller diameter $D_7$ at the distal end 302b.

Figure 3B:
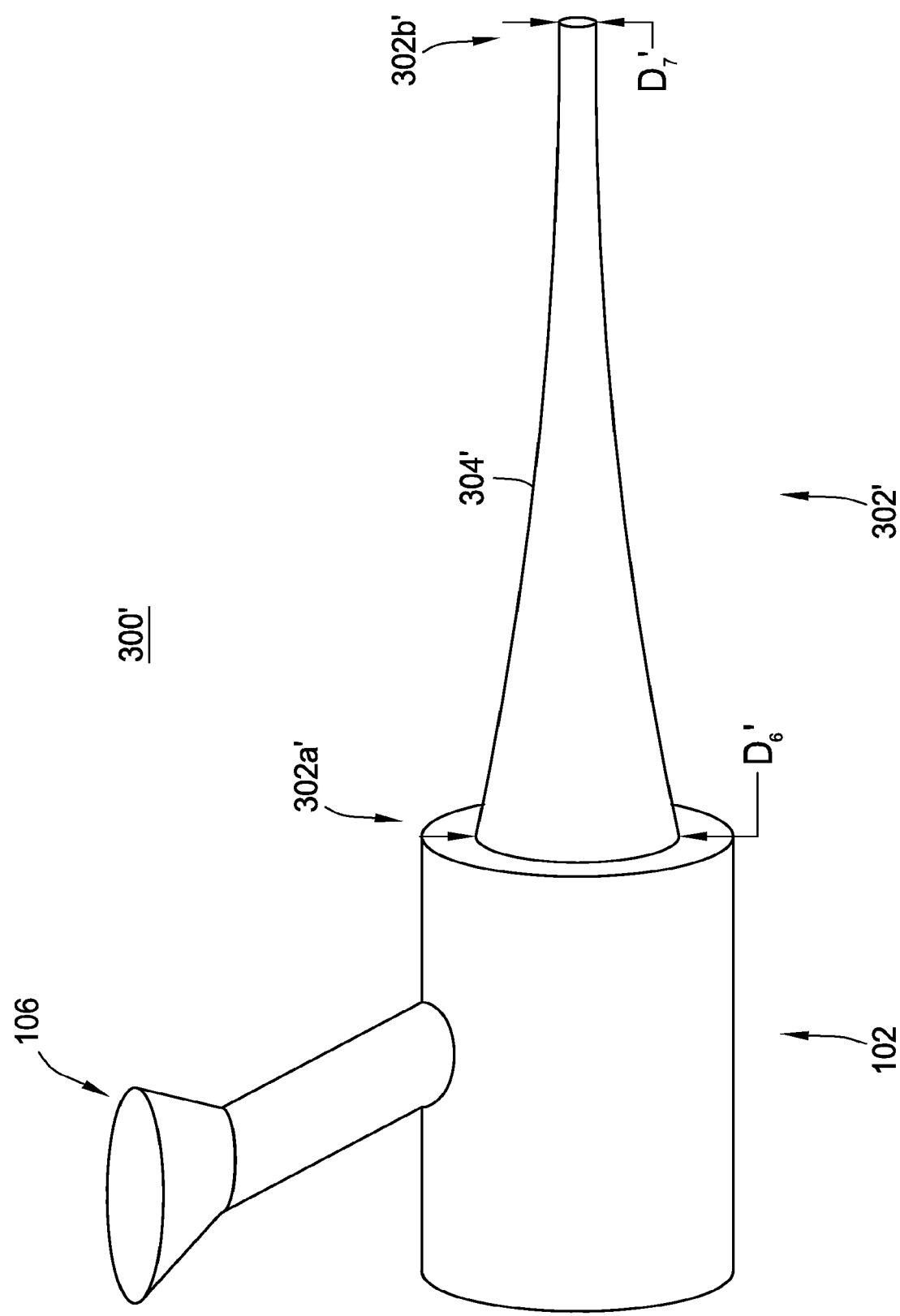
FIG. 3B shows a perspective view of an endoscope with a non-uniformly tapered working section, according to certain embodiments of the present disclosure.

Referring to FIG. 3B, according to some implementations, the working section 302 of FIG. 3A can instead have a non-uniform tapered outer surface, as shown by the endoscope 300' having the working section 302' with the non-uniform tapered outer surface 304'. Although the working section 302' includes a non-uniform tapered outer surface 304', according to some implementations, the proximal end 302a' of the working section 302' can have the same diameter $D_6$ as the proximal end 302a of the working section 302a. Further, the distal end 302b' of the working section 302' can have the same diameter $D_7$ as the distal end 302b of the working section 302b. Alternatively, the diameters can be different, such as the diameters $D_6'$ and $D_7'$ of the proximal end 302a' and distal end 302b' being larger or smaller than the diameters $D_6$ and $D_7$, respectively. The non-uniform taper can have various geometries, such as a parabolic taper as shown in FIG. 3B, that tapers from the largest diameter at the proximal end 302a' to the smallest diameter at the distal end 302b'.

FIG. 4A shows an endoscope 400, according to additional aspects of the present disclosure. The endoscope 400 is similar to the endoscope 300 of FIG. 3A but differs in that the endoscope 400 includes a working section 402 having an outer surface 404 with a first tapered portion and second non-tapered portion. Specifically, the endoscope 400 includes a working section 402 that includes a proximal end 402a and a distal end 402c. The working section 402 further includes a point 402b between the proximal end 402a and the distal end 402c, which separates the first tapered portion from the second non-tapered portion. The outer surface 404 of the working section 402 is tapered from the proximal end 402a to the point 402b. From the point 402b to the distal end 402c, the outer surface 404 of the working section 402 has a constant diameter. The proximal end 402a of the working section 402 has a diameter $D_8$, and the point 402b and the distal end 402c of the working section 402 have a diameter $D_9$. The diameter $D_8$ of the proximal end 402a is greater than the diameter $D_9$ of the point 402b and the distal end 402b. Despite having the constant diameter from the point 402b to the distal end 402c, the endoscope 400 can exhibit the same amount or less bending and/or flexing than an endoscope with the same length working section but with a constant diameter greater than the diameter $D_9$, or the endoscope 400 can exhibit the same amount or less bending and/or flexing than an endoscope with a shorter length working section but with a constant diameter $D_9$, based on the proximal end 402a having a larger diameter than the endoscope.

Figure 4B:
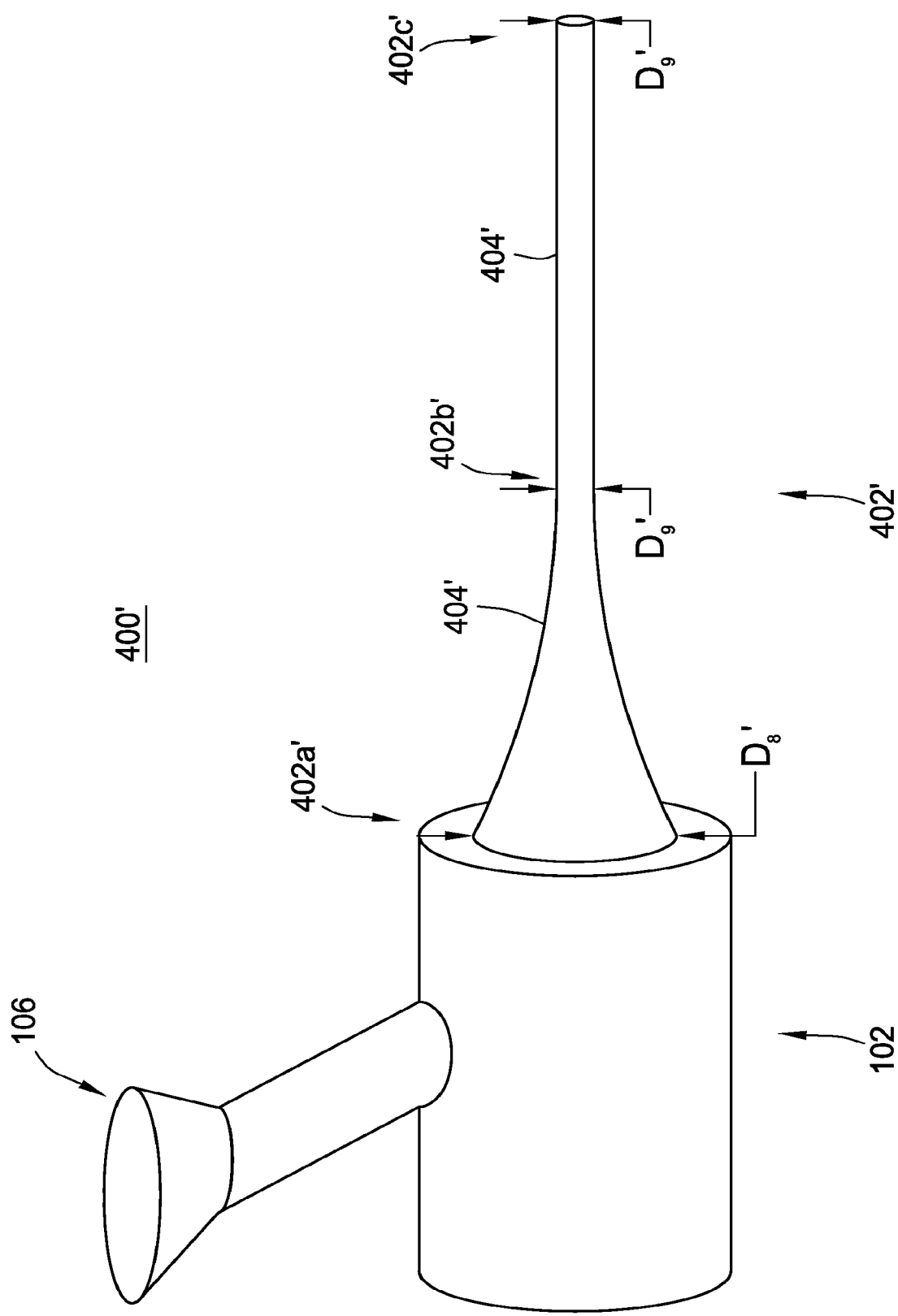
FIG. 4B shows a perspective view of an endoscope with a partially and non-uniformly tapered working section, according to certain embodiments of the present disclosure.

According to some implementations, and as shown in FIG. 4A, the outer surface 404 of the working section 402 from the proximal end 402a to the point 402b has a uniform taper. Alternatively, according to some implementations, and as shown in FIG. 4B, a first portion of the outer surface 404 of the working section 402 of FIG. 4A can instead have a non-uniform taper, as shown by the first portion of the outer surface 404' of the working section 402' having the proximal end 402a', the point 402b' and the distal end 402c' in FIG. 4B. Similar to FIG. 4A and as described herein, although the working section 402' includes a non-uniform taper, according to some implementations, the proximal end 402a' of the working section 402' can have the same diameter $D_8$ as the proximal end 402a of the working section 402a. Further, the point 402b' and the distal end 402c' of the working section 402' can have the same diameter $D_9$ as the distal end 402b' of the working section 402'. Alternatively, the diameters can be different, such as the diameters $D_8'$ and $D_9'$ of the proximal end 402a' and distal end 402b' being larger or smaller than the diameters $D_8$ and $D_9$, respectively. The non-uniform taper can have various geometries, such as a parabolic taper as shown in FIG. 4B, that tapers from the largest diameter at the proximal end 402a' to the smallest diameter at the distal end 402b'.

The principles described and illustrated above with respect to the working sections of FIGS. 1-4B can be modified and/or combined according to various different combinations, without departing from the spirit and scope of the present disclosure. By way of example, and without limitation, one or more of the sections of FIGS. 1 and 2 can be tapered according to the tapered working sections of FIGS. 3A-4B. For example, the middle section 204b of the working section 202 can be uniformly or non-uniformly tapered from the diameter $D_3$ of the of the outer surface 206a of the proximal section 204a to the diameter $D_5$ of the outer surface 206c of the distal section 204c, rather than having the step 208a from $D_3$ to $D_4$ and then the step 208b from $D_4$ to $D_5$. Further, although the transitions from the sections shown in FIGS. 1 and 2 are steps, according to some implementations, one or more of the transitions can be gradual or tapered transitions from one section to the next section. Such a gradual transition can eliminate, for example, possible sharp corners resulting from an abrupt transition between sections.

According to some implementations, although the outer diameters of the working sections have multiple diameter sections, the inner diameters of the working sections can have a constant diameter. Alternatively, according to some implementations, the inner diameters of the working sections can have multiple diameters to match the multiple diameters of the outer surfaces of the working sections.

Figure 5A:
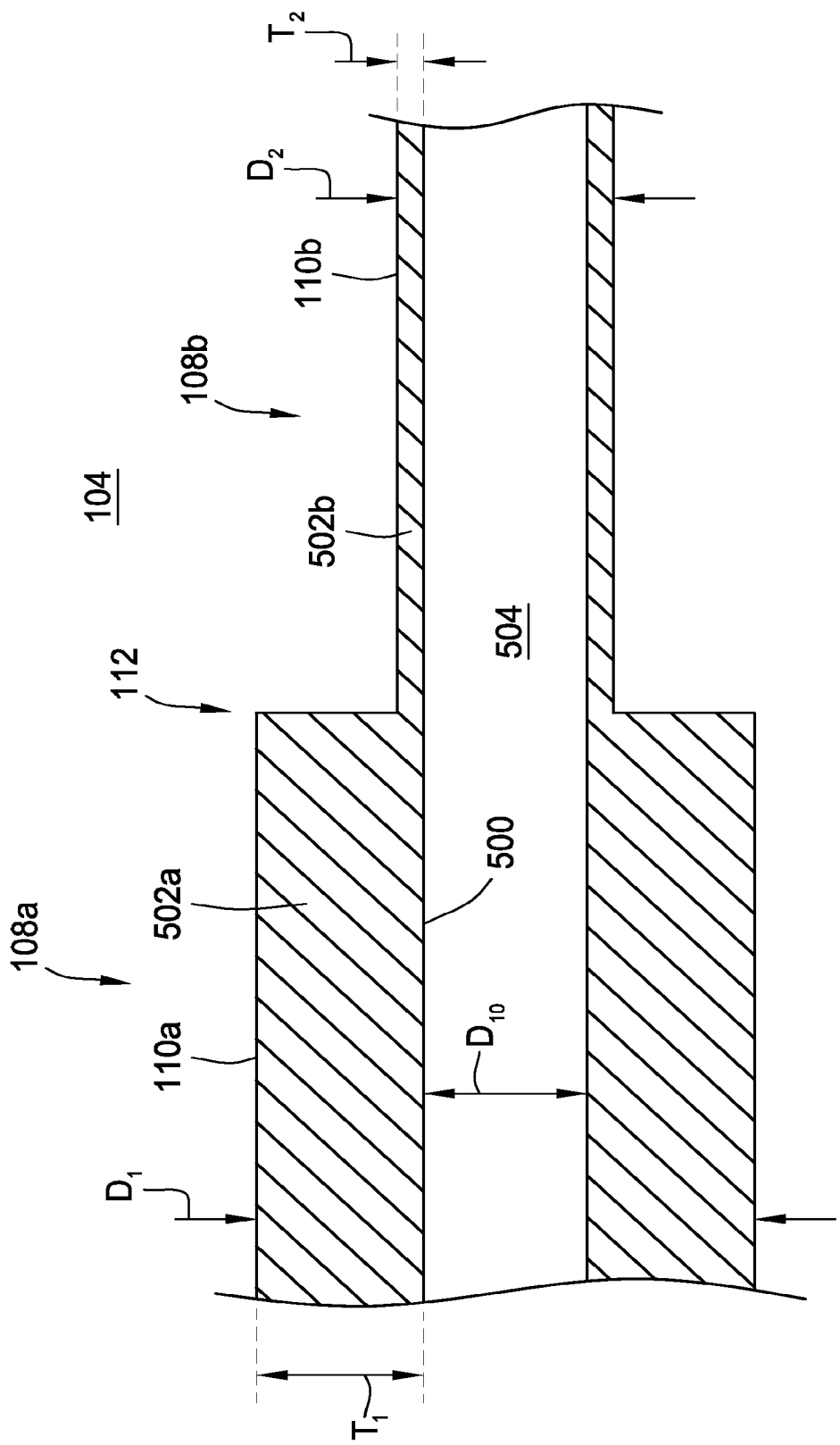
FIG. 5A shows a cross-section view of an endoscope with a multiple diameter working section, according to certain embodiments of the present disclosure.

Referring to FIG. 5A, FIG. 5A shows a cross-section view of an endoscope with a multiple diameter working section, according to aspects of the present disclosure. For example, FIG. 5A shows a cross-section view of the working section 104 of the endoscope 100 of FIG. 1. As shown, the working section 104 includes the access section 108a and the operative section 108b. The outer surface 110a of the access section 108a has the diameter $D_1$, and the outer surface 110b of the operative section 108b has the diameter $D_2$, with the step 112 in the diameters.

The working section 104 also includes an inner surface 500. The diameter $D_{10}$ of the inner surface 500 is constant along the length L of the working section 104. Accordingly, the access section 108a includes a wall 502a defined by the outer surface 110a and the inner surface 500 that has a thickness $T_1$, and the operative section 108b includes a wall 502b defined by the outer surface 110b and the inner surface 500 that has a thickness $T_2$. Thus, although the outer surfaces 110a and 110b of the working section 104 can have a step 112 in diameter, the inner surface 500 of the working section 104 can have a constant diameter along the entire length of the working section 104 such that the working section 104 is defined by walls (e.g., 502a and 502b) that have varying thicknesses.

The inner surface 500 of the working section 104 defines a channel or lumen 504 within the working section 104. As discussed above, the working section 104 can accept various instruments and/or house various components in the channel or lumen 504.

Figure 5B:
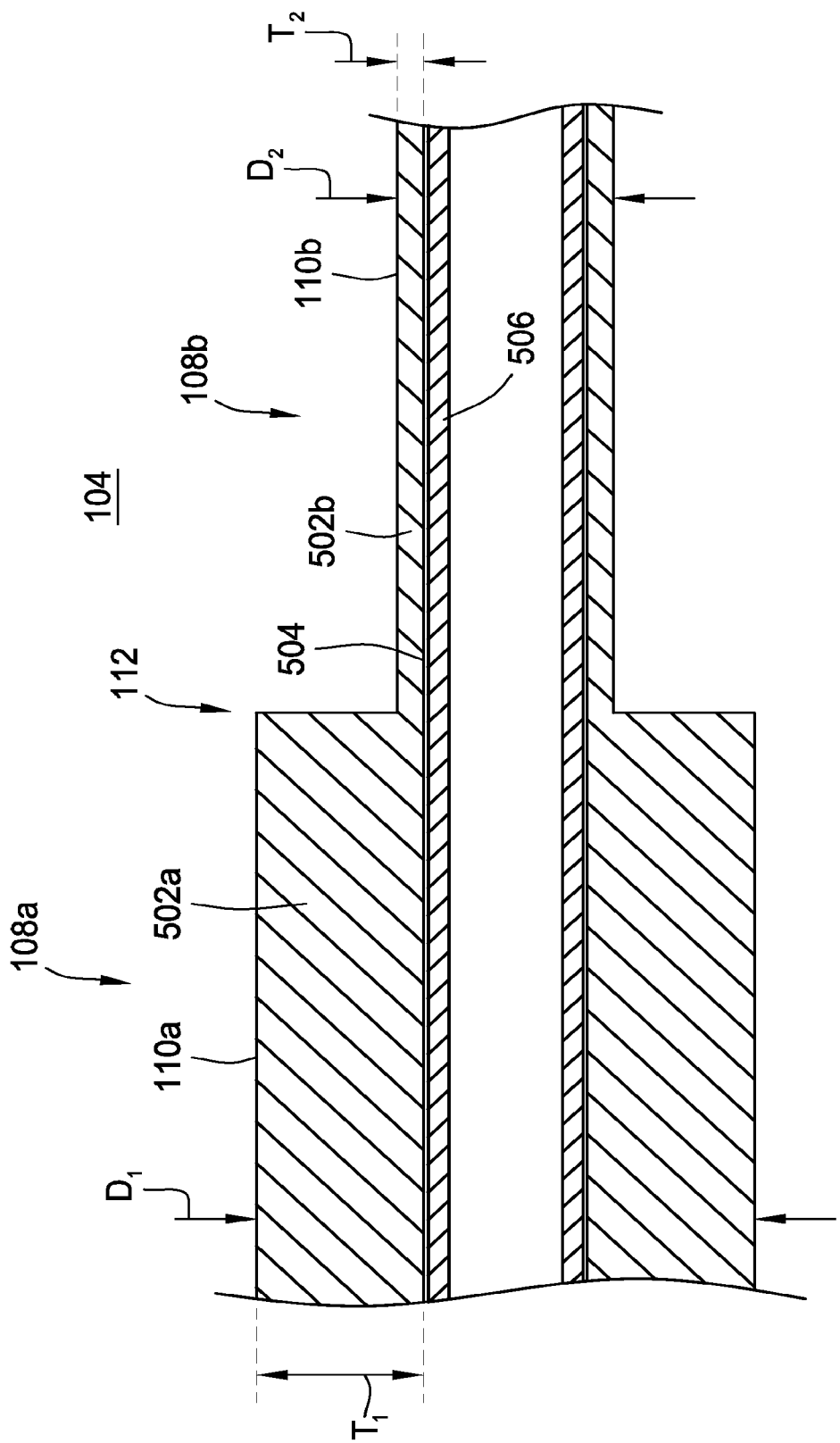
FIG. 5B shows a cross-section view of the endoscope of FIG. 5A with an instrument inserted therein, according to certain embodiments of the present disclosure.

Referring to FIG. 5B, FIG. 5B shows an instrument 506 inserted within the working section 104 through the channel 504. By way of example, and without limitation, the instrument 506 can be any instrument related to the endoscopy arts, such as a tissue removal device, a flexible or an inflexible optical system, etc. The instrument 506 has an outer diameter just slightly smaller than the diameter $D_{10}$ of the inner surface 500 defining the channel 504 to enable the instrument 506 to be inserted or positioned therein. According to some implementations, the instrument 506 (or components) can be affixed to the inside of the working section 104 within the channel 504 such that the instrument 506 is designed to not be removable. Alternatively, the instrument 506 (or components) can be removable within the channel 504 to enable various instruments and/or components to be inserted and removed, such as during a procedure and for various different functionalities.

Based on the step 112 in diameter of the working section 104, although the instrument 506 within the working section 104 has a constant diameter, forces applied to the distal end 104b of the working section 104 cause the operative section 108b of the working section 104 to bend less or not at all as compared to a working section of a same length as the working section 104. Thus, the instrument 506 is protected within the working section 104 from forces on the working section 104 at least partially by the multiple diameters of the outer surfaces 110a and 110b and the shortened length of the smallest diameter portion, i.e., operative section 108b (e.g., which is the portion of the working section 104 most prone to bending as it has the smallest outer diameter). Moreover, because of the protection of the instrument 506 caused by the multiple diameters, the diameter of the instrument 506 can be reduced without experiencing an increase in the chances of the instrument 506 failing as a result of forces applied to the distal end 104b of the working section 104.

Figure 5C:
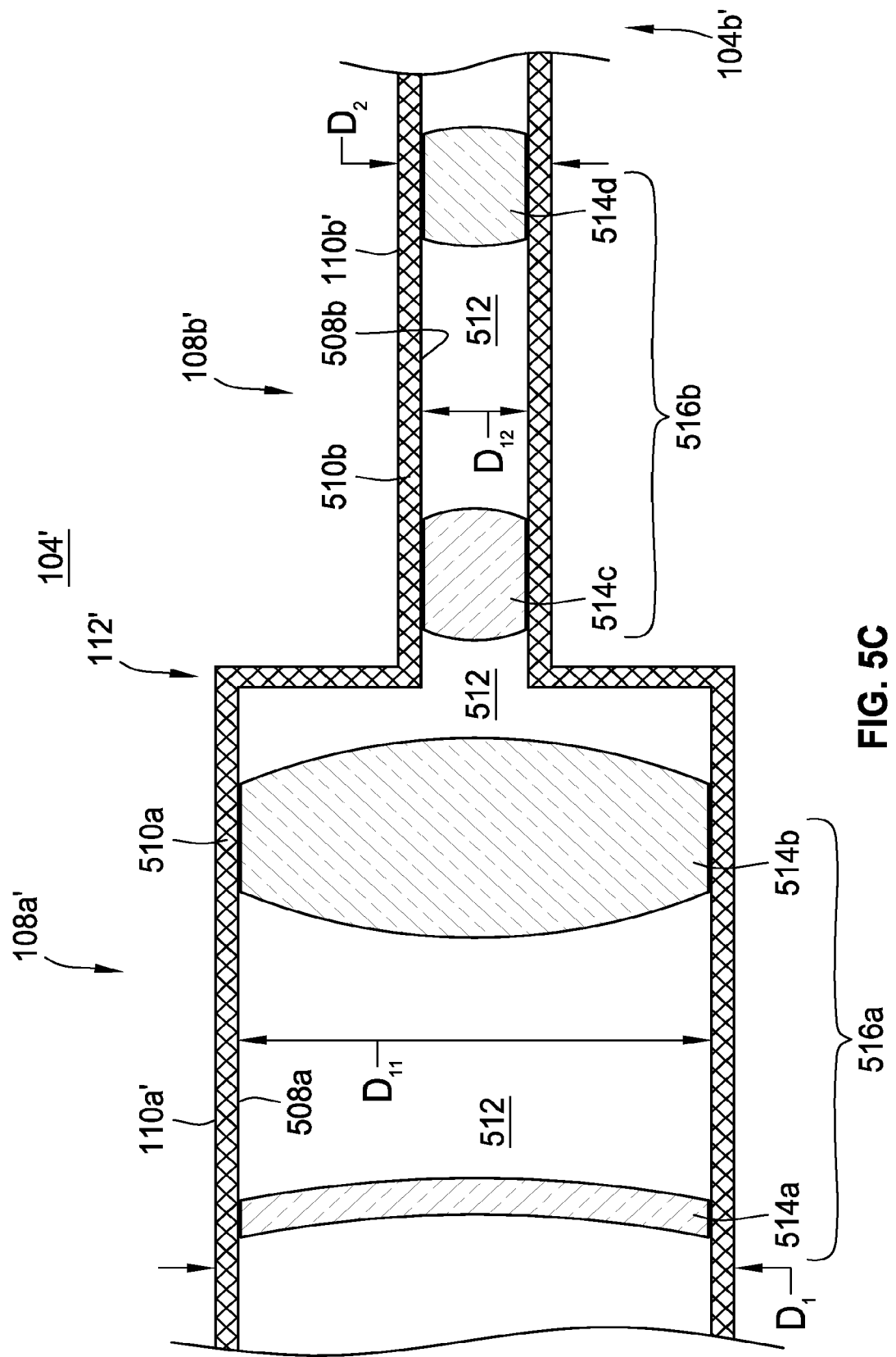
FIG. 5C shows a cross-section view of an endoscope with a multiple diameter working section, according to certain embodiments of the present disclosure.

Referring to FIG. 5C, FIG. 5C shows a cross-sectional view of an alternative version of the working section 104 of the endoscope 100 of FIG. 1, such as a working section 104', according to some aspects of the present disclosure. As shown, like the working section 104, the working section 104' includes the access section 108a' and the operative section 108b'. The outer surface 110a' of the access section 108a' has the diameter $D_1$ and the outer surface 110b' of the operative section 108b' has the diameter $D_2$, with the step 112' in the diameters. The access section 108a' also includes an inner surface 508a and the operative section 108b includes an inner surface 508b. The inner surface 508a of the access section 108a' has a diameter $D_{11}$ and the inner surface 508b of the operative section 108b' has a diameter $D_{12}$. Like the diameters of the outer surfaces 110a' and 110b', the diameters of the inner surfaces 508a and 508b also decrease towards the distal end 104b' of the working section 104'. Thus, the diameter $D_{11}$ of the inner surface 508a of the access section 108a' is greater than the diameter $D_{12}$ of the inner surface 508b of the operative section 108b'.

According to some implementations, the thickness of the wall 510a defined by the outer surface 110a' and the inner surface 508a of the access section 108a' can be the same thickness, a thicker thickness, or a thinner thickness than the thickness of the wall 510b defined by the outer surface 110b' and the inner surface 508b of the operative section 108b'. Further, similar to the outer surfaces 110a and 110b described above, although the transition between the inner surface 508a of the access section 108a' and the inner surface 508b of the operative section 108b' is shown as the step 112', according to some implementations, the transition can alternatively have a uniform or a non-uniform taper. Further, according to some implementations, although the inner surface 508a of the access section 108a' and the inner surface 508b of the operative section 108b' are shown as having a constant diameter $D_{11}$ and $D_{12}$, respectively, the diameters of one or more of the inner surfaces 508a and 508b can have a uniform or non-uniform taper.

The inner surfaces 508a and 508b of the access section 108a' and the operative section 108b' define a channel or lumen 512 through the working section 104'. The channel or lumen 512 enables one or more instruments to be inserted through the working section 104' and/or enables one or more components to be contained within the working section 104'. As described above, according to some implementations, the working section 104' can contain an optical system to enable a user to view into a patient during a procedure. According to some implementations, the optical system can be a fixed rod-lens optical system, as shown in FIG. 5C by a plurality of optical elements 514a-514d positioned along the channel 512.

Because the channel 512 includes multiple diameters, the instruments and/or components inserted through and/or contained within the channel 512 can also have multiple diameters along a length of the instrument and/or component. By way of example, and as shown in FIG. 5C, the optical elements 514a-514d of the rods-lens optical system can have, for example, two sections that correspond to the two sections of the working section 104'. Thus, the optical elements 514a-514d can be divided into a proximal section 516a formed of the optical elements 514a and 514b, and a distal section 516b formed of the optical elements 514c and 514d. The proximal section 516a, and the associated optical elements 514a and 514b, has a diameter slightly less than $D_{11}$ corresponding to the diameter of the inner surface 508a, and the distal section 516b, and the associated optical elements 514c and 514d, has a diameter $D_{12}$ corresponding to slightly less than the diameter $D_{12}$ of the inner surface 508b.

According to the optical elements 514a-514d of the rod-lens optical system having the sections with multiple diameters, the overall performance of the rod-lens optical system may be improved as compared to an optical system with a constant diameter of $D_{12}$. For example, the rod-lens optical system can have larger optics within the access section 108a', as compared to a rod-lens optical system within an endoscope with a constant, smaller inner diameter. The larger optics can provide better overall performance as compared to an optical system having smaller optics. Moreover, because of the multiple diameters, the rod-lens optical system in the endoscope 100' can bend and/or flex less to reduce the chances of damaging the rod-lens optical system.

Other instruments and/or components within the working section 104' can have the same configuration of the rod-lens optical system. For example, a tissue removal device can have a larger diameter at a proximal end and a smaller diameter at a distal end to correspond with the dimensions of the working section 104'. The larger diameter at the proximal end can increase the structural rigidity of the tissue removal device as compared to a tissue removal device having the same length and with a constant, smaller diameter. Yet, the diameter of the distal end of the tissue removal device can be smaller than the distal end of a tissue removal device having a constant diameter.

Although the working sections 104 and 104' are described above as having a single channel (e.g., channel 504 or channel 512), according to some implementations, the working sections described herein can include multiple channels (e.g., two channels, three channels, etc.). Accordingly, one or more of the multiple channels can have a constant diameter, one or more of the multiple channels can have multiple diameters, or all of the multiple channels can have constant or multiple diameters. By way of example, the working section 104 of the endoscope 100 can include two channels, where a first channel houses a rod-lens optical system and a second channel enables a tissue removal device to pass therethrough. In various embodiments, of the channels can have a constant diameter, both of the channels can have multiple diameters, and one channel can have a constant diameter while the other channel has multiple diameters.

In addition to instruments and/or components inserted through and/or contained within the working section 104 having multiple diameters, components that attach to the endoscope 100 and that surround the outside of the working section 104 can also have multiple diameters.

Figure 5D:
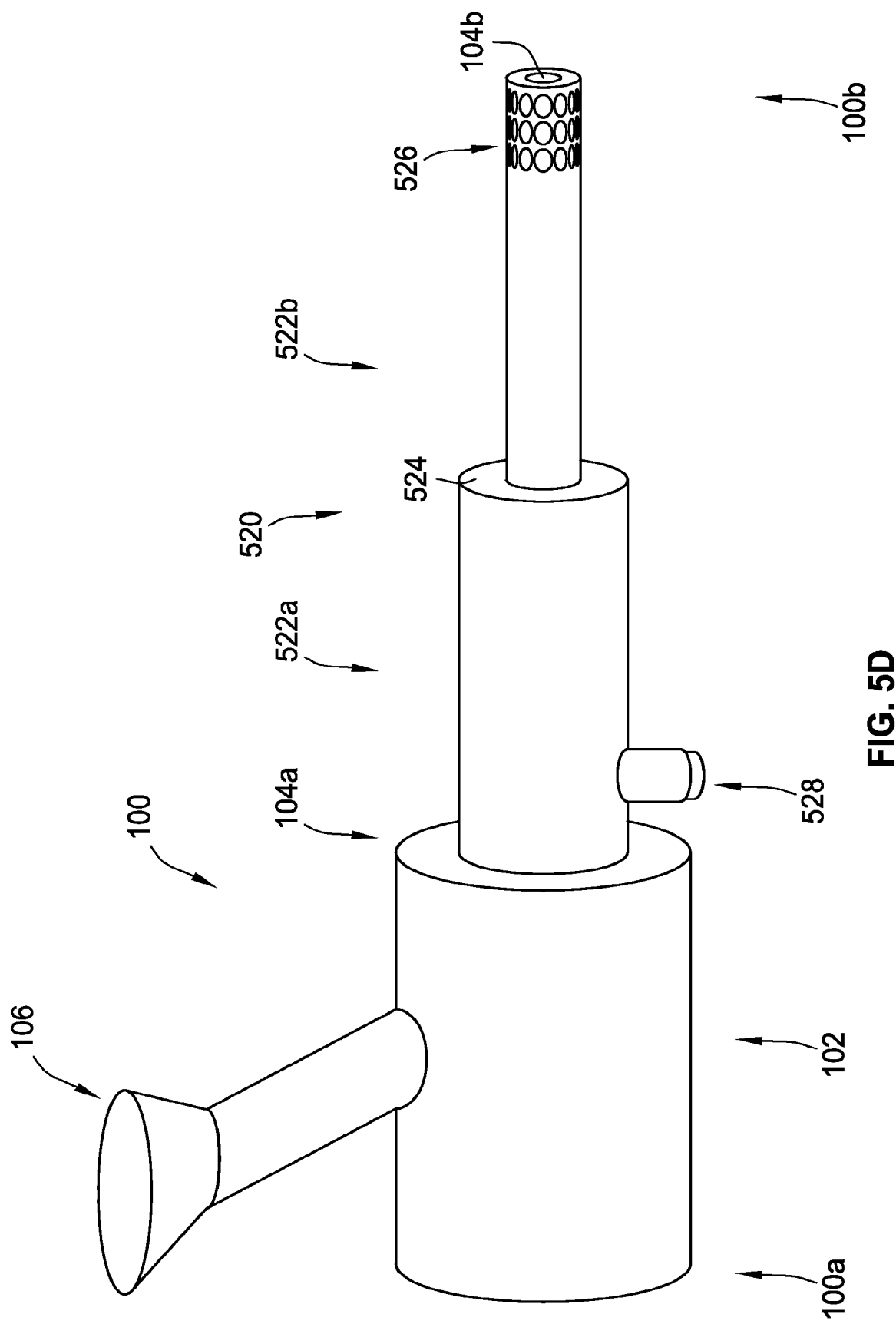
FIG. 5D shows a perspective view of an endoscope with a multiple diameter component surrounding the working section, according to certain embodiments of the present disclosure.

FIG. 5D shows the endoscope 100 with a component, particularly a sheath 520, attached and surrounding the working section 104 (covered by sheath 520), according to aspects of the present disclosure. The sheath 520 is a single, monolithic component that, similar to the working section 104, includes an access section 522a and an operative section 522b. The access section covers and corresponds to the access section 108a of the working section 104, and the operative section 522b covers and corresponds to the operative section 108b of the working section 104. Also similar to the working section 104, the sheath 520 includes a step 524 in diameter that corresponds to the step 112 in diameter of the working section 104. Thus, the outer diameter of the access section 522a is larger than the outer diameter of the operative section 522b.

The sheath 520 may further include, for example, inlets 526 to enable fluid and material to pass through the sheath 520 and travel back towards, for example, an outlet 528 of the sheath 520 through an outlet channel formed between an inner surface of the sheath 520 and the outer surfaces 110a and 110b of the working section 104. Such a configuration can be used, for example, during hysteroscopy procedures to remove fluid and material (e.g., cut and detached tissue, like fibroid tissue) from inside the uterus.

By the sheath 520 having a step in diameter, the sheath 520 has the same benefits discussed above with respect to the working section 104 having a step in diameter. For example, the outer diameter of the sheath 520 at the operative section 522b can be smaller than a sheath without the operative section 522b bending/flexing more in response to the same amounts of force applied to the sheath 520. Thus, the endoscope 100 with the attached sheath 520 can access areas inside a patient that an endoscope may not typically be designed to reach, such as areas reached without the patient being under anesthesia, or reach areas with less associated discomfort during and after the procedure.

Although the sheath 520 is illustrated and described above with respect to FIG. 5D, the sheath 520 is just one example of a component that can attach to the endoscope 100 and have multiple diameters for the outer surface. The same configuration can be used with other components that can be used with an endoscope, such as a cannula. Moreover, although the sheath 520 is illustrated and described above with respect to the working section 104, the configuration of the sheath 520 can change to correspond to any of the possible configurations of the working sections discussed herein, without departing from the spirit and scope of the present disclosure. Moreover, alternatively, one or more components and/or instruments can be attached to the endoscope 100 that do not have multiple diameters for the outer surface.

As discussed above, endoscopes are inserted through an entry point into a patient. The entry point can be an incision or an orifice, or through another instrument (e.g., cannula) that is inserted in an incision or an orifice. For certain procedures, such as a hysteroscopy procedure, the endoscope must be sufficiently long to reach the site associated with the procedure (e.g., uterus). For these procedures, the first (initial) entry point into the patient may be considered as the initial entry point of multiple entry points prior to the distal end of the working section reaching the site. By way of example, and without limitation, in the case of a hysteroscopy, the initial entry point may be the external orifice of the vagina. A subsequent entry point within the patient is the transition between the vaginal cavity and the cervix, also referred to as the external cervical os. A final entry point within the patient is the transition between the cervix and the uterus, also referred to as the internal cervical os.

Of these three orifices, the internal cervical os is the smallest entry point. Depending on the patients' pain tolerance thresholds and anatomical dimensions, the internal cervical os cannot be dilated beyond certain limits without the patients experiencing more than tolerable levels of discomfort, such as levels of discomfort for which anesthesia normally is used. According to some guidelines, six mm has been found to be an example of the dilation limit; however, this value can vary between patients. Accordingly, some endoscopes that are used to pass through the internal cervical os are designed such that the diameter along the entire length of the working section is small enough to pass through the internal cervical os without causing greater than tolerable levels of discomfort. This presents an issue for endoscopes because the entire length of the working sections at such small diameters may enable bending/flexing beyond threshold levels and cause damage to components and/or instruments inserted therethrough or contained therein.

In contrast to some endoscopes, and as applied to the endoscope 100 which is fabricated according to certain embodiments of the present disclosure, as an example, the diameter $D_2$ of the operative section 108b can be less than the maximum diameter of the internal cervical os, and the diameter $D_1$ of the access section 108a can be larger than the maximum diameter of the external cervical os without presenting similar issues as described above with respect to the working section 104 bending/flexing beyond threshold levels. For example, a vagina in a relaxed state can have an inner diameter of twenty mm. Thus, the diameter $D_1$ of the access section 108a can be about twenty mm without causing more than tolerable levels of discomfort with the access section 108a inserted into the vagina. Thus, for the same length of a working section, the length of the smallest diameter portion, i.e., the length of the operative section 108b, is shorter for the endoscope 100 as compared to a conventional endoscope. Accordingly, the same amount of force applied to the operative section 108b causes the operative section 108b to bend and/or flex less than a conventional endoscope for the operative section 108b having the same diameter, or even a smaller diameter, than the conventional endoscope.

Figure 6A:
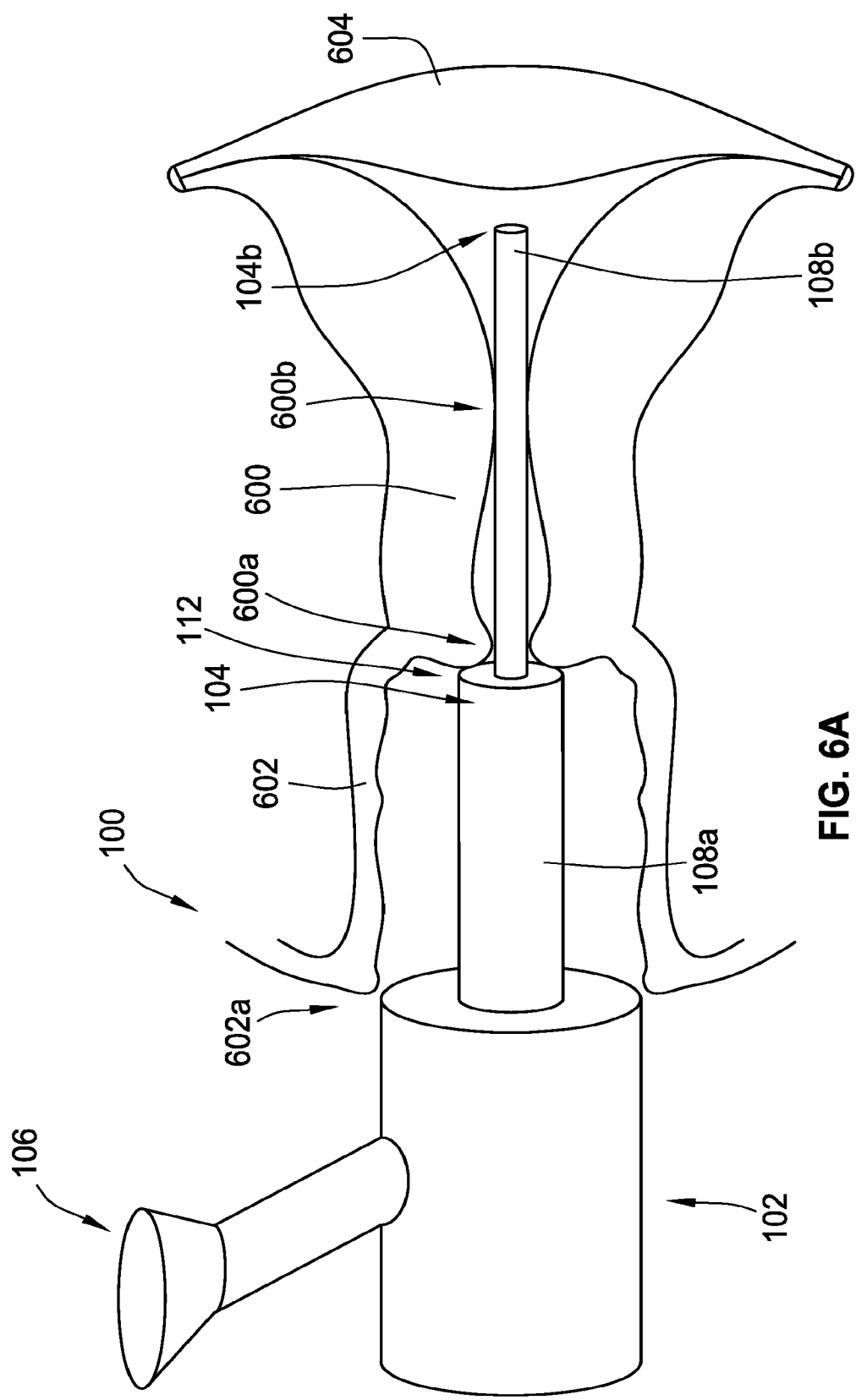
FIG. 6A shows a perspective view of an endoscope with a multiple diameter working section inserted within a uterine cavity, according to certain embodiments of the present disclosure.

Referring to FIG. 6A, FIG. 6A shows a view of the endoscope 100 inserted into a uterine cavity, according to some aspects of the present disclosure. As shown, the step 112 between the access section 108a and the operative section 108b of the working section 104 can be formed to correspond with the location of the external cervical os 600a with the distal end 104b of the working section 104 inserted through the orifice 602a of the vagina 602, through the internal cervical os 600b, and able to reach a site within the uterus 604. Thus, the length of the operative section 108b can be formed to correspond with an average length of the cervix 600 and the uterus 604 for the operative section 108b to be able to extend through the cervix 600 and access into the uterus 604. Similarly, the length of the access section 108a can be formed to correspond with an average length of the vagina 602 and account for additional space external to the vagina 602 for a user to grasp and manipulate the endoscope 100 and account for variations in users' body-mass-indices.

Based on a diameter of a relaxed vagina of, for example, twenty mm, the diameter $D_1$ of the access section 108a can be about twenty mm. Further, based on a threshold opening of the internal cervical os of, for example, six mm, the diameter $D_2$ of the operative section 108b can be less than about six mm because the length of the operative section 108b does not span the entire length of the working section 104. Despite the smaller diameter $D_2$ of the operative section 108b, the shorter length of the operative section 108b still limits the amount bending and/or flexing of the operative section 108b to less than threshold levels related to causing damage to elements and/or instruments within the working section 104.

Although the endoscope 100 of FIG. 1 is illustrated within the vaginal cavity of FIG. 6A, the step 112 between the access section 108a and the operative section 108b can be modified to be tapered to remove, for example, any sharp corners associated with the step 112 that may contribute to discomfort for the patient.

Figure 6B:
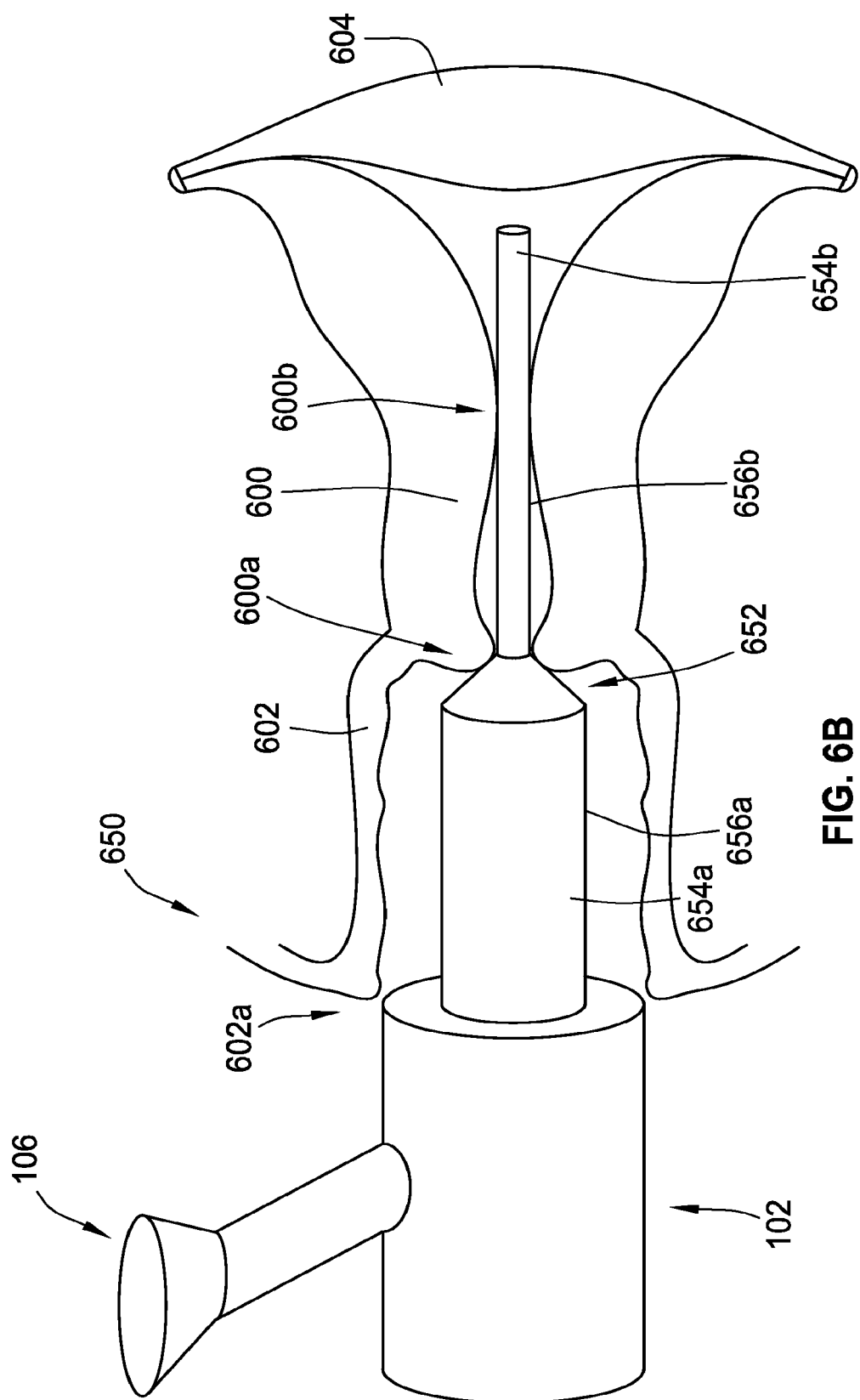
FIG. 6B shows a perspective view of an endoscope with a multiple diameter working section inserted within a uterine cavity, according to certain embodiments of the present disclosure.

Referring to FIG. 6B, an endoscope 650 is shown in FIG. 6B that is similar to the endoscope 100 of FIGS. 1 and 6A, but that the endoscope 650 has a transition section 652 between an access section 654a and an operative section 654b. The transition section 652 provides for a gradual transition between an outer surface 656a of the access section 654a and the outer surface 656b of the operative section 654a. This is in contrast to 6A where the transition is a stepped transition at step 112, that is, in FIG. 6B, the transition section 652 provides a smoothed transition between sections 654a and 654b. The transition section 652 may comprise one or more sections of varying diameters and transitions, depending upon the embodiment.

Moreover, any of the above-described endoscopes can be used for hysteroscopy procedures. According to some implementations, an endoscope, such as the endoscope 200, can be used for hysteroscopy. Accordingly, the diameter $D_3$ of the proximal section 204a can be designed to match the inner diameter of the vagina, the diameter $D_4$ of the middle section 204b can be designed to match the inner diameter of the cervix, and the diameter $D_5$ of the distal section 204c can be designed to be less than the diameter of the internal cervical os, such as, for example, about three to about six mm, so that the patient does not experience more than tolerable levels of discomfort. However, according to some implementations, the diameter $D_5$ of the distal section 204c can be designed to be larger, such as for procedures performed under anesthesia. By way of example, and without limitation, the diameter $D_5$ of the distal section 204c can be about seven mm, or larger, while still exhibiting less bending/flexing as compared to working sections of similar length and a constant diameter of seven mm in other endoscopes. Further, the transitions between the proximal section 204a and the middle section 204b, and the middle section 204b to the distal section 204c, can be tapered. Further, the lengths of the proximal section 204a, the middle section 204b, and the distal section 204c can be configured to match the inner dimensions of the vaginal cavity of, for example, an average adult female human. By way of example, the proximal section 204a can have a length of at least forty to about ninety-five mm, which is the average length of an adult female's vagina in a relaxed state, the middle section 204b can have a length of about twenty to about thirty mm, which is the average length of an adult female's cervix, and the distal section 204c can have a length of about fifty to about seventy mm, which is the average length of an adult female's uterus. According to some implementations, the length of the proximal section can be longer than ninety-five mm to account for additional depths created by patients with a higher body mass index.

In an embodiment, an endoscope comprising: a proximal end and a distal end; a housing at the proximal end of the endoscope; a working section coupled to and extending from the housing, the working section including a first section and a second section, wherein the first section is contiguous to the housing, and wherein the second section is at the distal end of the endoscope, an outer diameter of the first section is larger than an outer diameter of the second section; and an optical system positioned at least partially in the first section of the working section and at least partially in the second section of the working section. In an embodiment, the working section further includes a third section between the first section and the second section, and an outer diameter of the third section is less than the outer diameter of the first section and greater than the outer diameter of the second section. In an embodiment, the working section further includes a plurality of middle sections between the first section and the second section, and outer diameters of the middle sections progressively decrease from a proximal middle section contiguous to the first section to a distal middle section contiguous to the second section, wherein a diameter of the optical system positioned within the first section is larger than a diameter of the optical system positioned within the second section, and wherein the working section includes an operative channel configured to receive an instrument therein. In an embodiment, an outer surface of the instrument includes at least one step in diameter, and a location of the at least one step in diameter of the instrument corresponds to a distal end of the first section, the proximal end of the second section, or a combination thereof when the instrument is inserted within the operative channel of the working section. In an embodiment, the outer diameter of the second section is between about three millimeters and about seven millimeters, and the outer diameter of the first section corresponds to a diameter of a first surgical entry point through which the endoscope is inserted, and wherein the outer diameter of the second section corresponds to a second entry point in the patient through which the endoscope is finally inserted. The endoscope of claim 1, wherein the first section is configured to be inserted into a body cavity during a procedure based on a length of the second section as compared to a required insertion distance into the body to enable access to a site for the procedure.

In an embodiment, the optical system comprises a rod-lens optical system and the endoscope further comprises a sheath extending from the housing and including a first section and a second section, the first section of the sheath surrounding the first section of the working section, and the second section of the sheath surrounding the second section of the working section, an outer diameter of the first section of the sheath is larger than an outer diameter of the second section of the sheath. In an embodiment, the second section of the sheath includes a plurality of inlets, the first section of the sheath includes an outlet, and an inner surface of the sheath and an outer surface of the working section form a channel connecting the plurality of inlets with the outlet.

In an embodiment, an endoscope comprising: a housing; a working section extending from the housing and having an outer surface, the outer surface having a proximal end and a distal end, the proximal end is contiguous to the housing and having a first diameter, and the distal end having a second diameter, the first diameter is larger than the second diameter; and an optical system positioned in the working section such that the optical system extends between the proximal and distal ends of the working section, wherein the outer surface of the working section is tapered from the proximal end to the distal end, wherein the taper is uniform along the length of the outer surface. In an alternate embodiment, the taper is non-uniform along the length of the outer surface such that the outer surface has a curved profile, and in another alternate embodiment, the taper is parabolic. In an embodiment, the outer surface of the working section is tapered from the proximal end to a point along the outer surface between the proximal end and the distal end, and a diameter of the outer surface from the point to the distal end is constant, and the taper is uniform along the length of the outer surface from the proximal end to the point. In an alternate embodiment, the taper is non-uniform along the length of the outer surface from the proximal end to the point such that the outer surface has a curved profile between the proximal end and the point.

In an embodiment, the working section further includes an inner surface defining a channel, the optical system positioned in the channel, and the inner surface having a proximal end and a distal end, the proximal end of the inner surface having a third diameter and the distal end of the inner surface having a fourth diameter, wherein the third diameter is larger than the fourth diameter, wherein the third diameter and the fourth diameter are about equal, and wherein the inner surface of the working section is tapered from the proximal end of the inner surface to a point along the inner surface between the proximal end of the inner surface and the distal end of the inner surface, and a diameter of the inner surface from the point to the distal end is constant. In an embodiment, the taper is uniform along the length of the inner surface from the proximal end of the inner surface to the point. In an alternate embodiment, the taper is non-uniform along the length of the inner surface from the proximal end of the inner surface to the point. In an embodiment, the optical system is a rod-lens optical system.

Exemplary embodiments are specifically disclosed and variations, combinations, and/or modifications of the embodiments and/or features of the embodiments made by a person having ordinary skill in the art are within the scope of the disclosure. Alternative embodiments that result from combining, integrating, and/or omitting features of the embodiments are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). In some embodiments, "about" may refer to a measurement with a tolerance of +/−5% of the stated measurement. In another example, whenever a numerical range with a lower limit, $R_l$, and an upper limit, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of broader terms such as "comprises," "includes," and "having" should be understood to provide support for narrower terms such as "consisting of," "consisting essentially of," and "comprised substantially of." Accordingly, the scope of protection is not limited by the description set out above but is defined by the claims that follow, that scope including all equivalents of the subject matter of the claims. Each and every claim is incorporated into the specification as further disclosure, and each claim is an exemplary embodiment of the present invention.

Although described above primarily with respect to applications of an endoscope related to hysteroscopy, the dimensions of the endoscope can be modified according to other procedures and based on the anatomical dimensions within the patient associated with the procedures, without departing from the spirit and scope of the present disclosure.

While the present disclosure has been described with reference to one or more particular implementations, those skilled in the art will recognize that many changes may be made thereto without departing from the spirit and scope of the present disclosure. The above described implementations, and obvious variations thereof, are contemplated as falling within the spirit and scope of the disclosure.

What is claimed is:
1. An endoscope comprising:
   a handle having a first outer diameter;
   an access section extending distally from the handle, the access section having a second outer diameter less than the first outer diameter of the handle and having a first wall having a first thickness;
   an operative section extending distally from the access section, the operative section having a third outer diameter less than the second outer diameter of the access section and having a second wall having a second thickness less than the first thickness of the first wall of the access section, wherein the third outer diameter of the operative section is constant along an entire length of the operative section;
   wherein an inner surface of the access section defines an access lumen having a first inner diameter, and wherein an inner surface of the operative section defines an operative lumen having a second inner diameter less than the first inner diameter of the access section;
   a first optical element positioned in the access section and having an outer diameter corresponding to the first inner diameter of the access lumen;
   a second optical element positioned in the operative section and having an outer diameter corresponding to the second inner diameter of the operative lumen; and
   a sheath surrounding the access section and the operative section and forming a fluid channel between an inner surface of the sheath and outer surfaces of the access section and the operative section, wherein the sheath includes:
a proximal portion having a proximal outer diameter corresponding to the second outer diameter of the access section; and
a distal portion having a distal outer diameter corresponding to the third outer diameter of the operative section.

2. The endoscope of claim 1, wherein the first inner diameter of the access lumen of the access section is constant along an entire length of the access section.

3. The endoscope of claim 1, wherein the second inner diameter of the operative lumen of the operative section is constant along an entire length of the operative section.

4. The endoscope of claim 1, further comprising a transition section between the handle and the access section providing a gradual transition between an outer surface of the handle and an outer surface of the access section.

5. The endoscope of claim 1, further comprising a transition section between the access section and the operative section providing a gradual transition between an outer surface of the access section and an outer surface of the operative section.

6. The endoscope of claim 1, further comprising:
a first transition section between the handle and the access section providing a gradual transition between an outer surface of the handle and an outer surface of the access section; and
a second transition section between the access section and the operative section providing a gradual transition between the outer surface of the access section and an outer surface of the operative section.

7. The endoscope of claim 1, wherein the second outer diameter is 20 mm.

8. The endoscope of claim 1, wherein the sheath includes a transition section between the proximal portion of the sheath and the distal portion of the sheath providing a gradual transition between an outer surface of the proximal portion of the sheath and an outer surface of the distal portion of the sheath.

9. The endoscope of claim 1, wherein the sheath includes an inlet configured to enable delivery of fluid and material through the fluid channel defined between the inner surface of the sheath and the outer surfaces of the access section and the operative section.

10. The endoscope of claim 1, wherein the access section includes a distal end and wherein forces applied to the distal end of the access section cause the endoscope to bend less than forces applied to the operative section.

11. The endoscope of claim 1, wherein at least one of the first optical element or the second optical element is a lens.

12. The endoscope of claim 1, wherein the second outer diameter corresponds to a diameter of a first surgical entry point through which the endoscope is inserted, and wherein the third outer diameter corresponds to a second entry point through which the endoscope is inserted.

13. The endoscope of claim 1, wherein the distal outer diameter of the distal portion of the sheath is constant along an entire length of the distal portion of the sheath.

* * * * *